United States Patent [19]

Takahashi et al.

[11] Patent Number: 4,677,066

[45] Date of Patent: Jun. 30, 1987

[54] METHOD FOR PROMOTING FUSION OF PLANT PROTOPLAST

[75] Inventors: Shigeru Takahashi; Yasuhiro Maeda, both of Otake, Japan

[73] Assignee: Mitsui Petrochemical Industries, Ltd., Tokyo, Japan

[21] Appl. No.: 564,899

[22] Filed: Dec. 23, 1983

[30] Foreign Application Priority Data

Dec. 27, 1982 [JP] Japan .............................. 57-227020
May 23, 1983 [JP] Japan .............................. 58-89192
May 24, 1983 [JP] Japan .............................. 58-90001

[51] Int. Cl.$^4$ ..................... C12N 15/00; C12N 5/00
[52] U.S. Cl. ............................ 435/172.2; 435/240; 935/94
[58] Field of Search ............. 435/172.2, 240, 241; 935/91, 94, 95, 98

[56] References Cited

FOREIGN PATENT DOCUMENTS

| 2842179 | 4/1980 | Fed. Rep. of Germany | 435/172.2 |
|---|---|---|---|
| 0068790 | 4/1982 | Japan | 435/240 |
| 0071887 | 4/1983 | Japan | 435/240 |
| 0076092 | 5/1983 | Japan | 435/240 |
| 1310119 | 3/1973 | United Kingdom | 435/172.2 |

OTHER PUBLICATIONS

Miller et al., 1973, "Plant Protoplast Culture", in *Tissue Culture Methods and Applications*, Academic Press, pp. 500–505.
Gamborg, 1976, "Somatic Cell Hybridization by Protoplast Fusion and Morphogenesis", in *Plant Tissue Culture & Its Biotechnological Application*, pp. 287–301.
Eriksson, 1976, "Technical Advances in Protoplast Isolation and Culture", in *Plant Tissue Culture and its Biotechnological Application*, pp. 316–322.
K. K. Kartha et al., MPC, Ltd. Iwakuni, Can. J. Bot., vol. 52, 1974, "Fusion of Rapeseed and Soybean Protoplasts and Subsequent Division of Heterokaryonytes", pp. 2–5.
F. Constabel et al., MPC, Ltd. Iwankuni, Z. Pflanzenphysiol. Bd. 79. S. 1–7., 1976, "Cell Division of Intergeneric Protoplast Fusion Products", pp. 6–12.
K. N. Kao and M. R. Michayluk, Planta (Berl.) 115, 355–367, (1974), "A Method For High—Frequency Intergeneric Fusion of Plant Protoplasts".
K. N. Kao, F. Constabel, M. R. Michayluk and O. L. Gamborg, Planta (Berl.) 129, 215–227, (1974), "Plant Protoplast Fusion and Growth of Intergeneric Hybrid Cells".
"The Expression of Tumour Markers in Intraspecific Somatic Hybrids of Normal and Crown Gall Cells from Nicotiana Tabacum", by Wullems et al., *Theor. Appln. Genet.* 56, 203–208, (1980).

*Primary Examiner*—Blondel Hazel
*Assistant Examiner*—David T. Fox
*Attorney, Agent, or Firm*—Cushman, Darby & Cushman

[57] ABSTRACT

A method for promoting fusion of plant protoplasts comprising the steps of; (a) treating the plant protoplasts with a fusion agent, and then (b) incubating the resultant plant protoplasts in an incubation medium having an osmotic pressure lower than that required for maintaining the plant protoplasts in a stable form. This effectively promotes the fusion of the plant protoplasts at a higher fusion rate in a wider range of plants.

15 Claims, No Drawings

METHOD FOR PROMOTING FUSION OF PLANT PROTOPLAST

BACKGROUND OF THE INVENTION

1. Field of the Invention

The present invention relates to a technique for cell fusion of plants, more particularly to a method for promoting fusion of plant protoplasts. The fused cells obtained by the cell fusion technique have new characteristics. Large-scale culture of the cells, for example, can provide a useful secondary metabolite product, or the fused cells differentiate to a useful new plant.

2. Description of the Prior Art

Rapid progress in tissue culture techniques has led to techniques for breeding new hybrid plants by artificial cell fusion. Breeding of hybrids of distantly related plants, hitherto thought impossible, is now feasible.

In cell fusion, the cell wall of the plant cells is removed by enzymes or a mechanical means, and the protoplasts are mixed to prepare fused cells. Simple mixing of the protoplasts, however, provides only a very low fusion rate. Therefore, various methods have been proposed for promoting the fusion of protoplasts.

The most preferable of these methods is to treat the protoplasts by a fusion agent prepared by a combination of polyethylene glycol and an alkaline aqueous solution of calcium chloride. It is possible to further improve the fusion by (1) raising the temperature, (2) using a decomposing agent for membrane protein of cell membrane, or (3) carrying out centrifugation.

While such methods may improve the fusion rate somewhat, the rate attained is still not satisfactory. Moreover, the methods cannot effect the cell fusion in some kind of plants.

Now, in the prior art cell fusion method, after the protoplasts are treated by the fusion agent, the fusing agent is removed by repeated washing with an aqueous solution. Then, the washed protoplasts are placed in the aqueous solution for storage.

To store the protoplasts in a stable form, it is necessary to raise the osmotic pressure of the aqueous solution carrying the protoplasts.

Toward this end use is made of an aqueous solution containing, for example, a sugar such as sucrose or glucose, a sugar alcohol such as mannitol or sorbitol, or an inorganic salt such as calcium chloride or potassium chloride as an osmotic pressure control agent. The osmotic pressure of the aqueous solution is preferably adjusted to between 12 kg/cm$^2$ and 30 kg/cm$^2$, more preferably to between 12 kg/cm$^2$ and 20 kg/cm$^2$.

SUMMARY OF THE INVENTION

Accordingly, an object of the present invention is to provide a movel method for promoting fusion of plant protoplasts, which provides a higher fusion rate and is applicable to a wider range of plants.

In accordance with the present invention, there is provided a method for promoting fusion of plant protoplasts comprising the steps of (a) treating the plant protoplasts with a fusing agent and then (b) incubating the treated plant protoplasts in an incubation medium having an osmotic pressure lower than that required for maintaining the plant protoplasts in a stable form.

In accordance with the preferred embodiment of the present invention, the incubation medium further can contain a fusion promoting agent. One type of the fusion promoting agent is a water-soluble protein and/or hydrophilic colloidal synthetic polymer. Another type of the fusion promoting agent is a water-soluble aprotic polar compound.

DESCRIPTION OF THE PREFERRED EMBODIMENTS

Plant

The present invention can be applied to all kinds of plants, for example, Lithospermum, ginseng, and other medicinal plants; carnations, roses, and other garden plants; cabbages, eggplants, and other vegetables; and rice, wheat, barley, and other grains.

The present invention can also be applied to intragenus or inter-genera cell fusion for all genera of plants, for example, Lithospermum such as *Lithospermum erythrorhizon Seib. et Zucc.*, Nicotiana such as *Nicotiana tabacum L.* var. *Samsum*, Coptis such as *Coptis japonica Makino*, Dianthus such as *Dianthus Caryophyllus L.*, Duboisia, such as *Duboisia leichharditii F. Muell*, Rosa such as *Rosa sp. cv. soraya*, Oryza such as *Oryza sativa L*, Triticum such as *Triticum durum*, and Zea such as *Zea mays L.*

Preparation of Plant Protoplasts

Plant protoplasts are prepared by treating a whole plant, a part of the same or plant cells with enzymes such as cellulose or pectinase or by an appropriate mechanical means to remove the cell wall. The resultant plant protoplasts are placed in an aqueous solution containing an osmotic pressure control agent to maintain them in a stable form until treatment with a fusion agent.

Treatment of Protoplasts with Fusing Agent

To treat the plant protoplasts, the fusion agent is added to the aqueous solution containing the plant protoplasts, or first the plant protoplasts are separated from the aqueous solution, and then the separated plant protoplasts are suspended in the aqueous solution containing the fusion agent. The treatment can be carried out in one or more steps.

Applicable fusion agents include synthetic polymer materials such as polyethylene glycol (PEG), polypropylene glycol (PPG), and polyvinyl alcohol (PVA); natural polymer materials such as dextrin and pectin; inorganic salts such as calcium chloride and sodium nitrate; and mixtures thereof. The preferable materials are PEG, PVA and dextrin, especially PEG. The PEG preferably has an average molecular weight of 1,500 to 7,500.

During the treatment, the plant protoplasts are first incubated in the aqueous solution containing the fusion agents at a relatively high osmotic pressure, preferably 12 kg/cm$^2$ to 40 kg/cm$^2$, to maintain them in a stable form. For this purpose, if necessary, an osmotic pressure control agent such as sugar, sugar alcohol, or inorganic salts is used.

The treatment is carried out at a temperature of 0° C. to 60° C., preferably 20° to 40° C.

Incubation at a lower osmotic pressure

According to the present invention, the plant protoplasts are then incubated at a lower osmotic pressure than the level required for maintaining the protoplasts in a stable form.

Generally, plant protoplasts cannot remain stable for a period of several days or more under an osmotic pressure of 10 kg/cm² or less. Plant protoplasts are relatively readily destroyed at an osmotic pressure of less than 9 kg/cm². In accordance with the present invention, the plant protoplasts are incubated at an osmotic pressure of not more than 10 kg/cm², preferably 2 kg/cm² to 10 kg/cm², for 5 minutes to 48 hours, preferably 10 minutes to 2 hours. The incubation time is selected, depending on the selected osmotic pressure, so that the plant protoplasts are sufficiently treated to promote cell fusion, but are not destroyed.

In the incubation, the plant protoplasts are placed in an incubation medium having a low osmotic pressure. For this purpose, various processes can be used. In one embodiment, water or an aqueous solution having a low osmotic pressure is mixed with the aqueous solution containing the fusing agent and plant protoplasts. In this case, the resultant mixture forms the incubation medium containing the plant protoplasts. The water or the aqueous solution having a low osmotic pressure can be mixed at once or step by step. The amount of the water or the aqueous solution having low osmotic pressure is selected depending on the desired osmotic pressure of the incubation medium. For example, 1 to $10^4$ parts by volume, especially 10 to $10^3$ parts by volume, of water or aqueous solution having a low osmotic pressure is mixed with 1 part by volume of the aqueous solution containing the fusion agent and plant protoplasts so that the resultant mixture has a desired osmotic pressure.

Alternatively, the plant protoplasts are separated from the aqueous solution containing the fusion agent, then the separated protoplasts are suspended in the incubation medium having a desired osmotic pressure.

To control an osmotic pressure or to protect protoplasts to be fused, sugars such as sucrose or glucose, sugar alcohols such as mannitol or sorbitol, inorganic salts such as calcium chloride or magnesium chloride, various kinds of nutrients for plant cell cultures, or mixtures thereof can be added to the incubation medium. Among these, sugar or an inorganic salt, especially calcium chloride or a combination of calcium chloride and sugar is preferable.

The coexistence of fusion promoting agents such as water-soluble proteins, and hydrophilic colloidal synthetic polymers, with the plant protoplasts in the incubation medium having a low osmotic pressure further promotes the cell fusion.

The water-soluble proteins include a serum protein such as albumin and globulin and an enzyme protein such as papain and bromelin. These proteins can be used singly or in combination. Among these proteins, serum protein, especially albumin or globulin, is preferable.

The hydrophilic colloidal synthetic polymers include polymers prepared by coating polyvinyl pyrrolidone, polyacrylamide, or other hydrophilic resin on fine particles of glass, silica, alumina, active carbon, or other insoluble material, and a synthetic polymer prepared from sucrose and epichlorohydrin and having a plurality of branched structures. The synthetic polymers can be used singly or in combination.

If necessary, both the water-soluble proteins and the hydrophilic colloidal synthetic polymers can be used simultaneously.

The incubation medium preferably contains the water-soluble proteins and/or the synthetic polymers in an amount of 0.001 to 10 parts by weight, more preferably 0.01 to 1 part by weight, per 100 parts by weight of the incubation medium containing the plant protoplasts. An amount of the water-soluble proteins and/or the synthetic polymers less than 0.001 parts by weight and more than 10 parts by weight reduces the effectiveness of the promotion of cell fusion.

The coexistence of one or more water-soluble aprotic polar compounds, as a fusion promoting agent, with the plant protoplasts in the incubation medium having a low osmotic pressure also further promotes the cell fusion.

The water-soluble aprotic polar compounds include, for example, sulfones such as sulforane and dimethyl sulfone; sulfoxides such as dimethyl sulfoxide and diethyl sulfoxide; amides such as N,N-dimethylformamide, N,N-diethylformamide, N,N-dimethylacetamide, N-methylpyrrolidone, N-ethylpyrrolidone, N-isopropylpyrrolidone, N-octylpyrrolidone, N-cyclohexylpyrrolidone, N-benzylpyrrolidone, polyvinyl-pyrrolidone, N-methyl-2-pyridone, and N-methyloxazolidone; phosphoric triamides such as hexamethylphosphoric triamide and hexaethylphosphoric triamide; and substituted ureas such as N,N,N',N'-tetramethylura and 1,3-dimethyl-2-imidazolidone. Among these, dimethylformamide, dimethyl sulfoxide, and dimethylacetamide are preferably used.

The water-soluble aprotic polar compounds can be used singly or in combination.

The incubation medium preferably contains the water-soluble aprotic polar compounds in an amount of 0.01 to 10 parts by volume, more preferably 0.1 to 5 parts by volume, per 100 parts by volume of the medium containing the plant protoplasts. An amount of the water-soluble aprotic polar compound less than 0.01 part by volume and more than 10 parts by volume reduces the effectiveness of the promotion of cell fusion.

Coexistence of the fusion promoting agents with plant protoplasts in the incubation medium can be achieved by various processes. For example, a predetermined amount of the fusion promoting agent can be directly added to the low osmotic pressure incubation medium containing the plant protoplasts. Alternatively, prior to the separated protoplasts are suspended in the incubation medium, the cell fusion promoting agent can be added to the medium. Moreover, in the embodiment wherein water or an aqueous solution having a low osmotic pressure is mixed with the aqueous solution containing the fusion agent and plant protoplasts, the fusion promoting agent can be added to the water or the aqueous solution having a low osmotic pressure.

The incubation is carried out at a temperature of 0° C. to 60° C., preferably 15° C. to 40° C.

In the practice of the present invention, other known methods can be used to promote cell fusion, for example, treatment of plant protoplasts at a high temperature (about 30° C. to 50° C.), treatment of plant protoplasts with a modifying agent for membrane protein of the cell membrane (for example, cytochalasin B and N-ethyl maleimide), or centrifugation (40XG to about 200XG).

After the treatment of the plant protoplasts by the method of the present invention, the plant protoplasts are separated from the low osmotic pressure medium, by a known means and, if necessary, again incubated in a culture medium having an osmotic pressure required to maintain the plant protoplasts in a stable form to reconstruct the cell walls. The resultant hybrid cells are then separated by a known means.

As described above, by incubating plant protoplasts in the incubation medium having an osmotic pressure lower than that required for maintaining the plant protoplasts, the cell fusion is effectively promoted.

EXAMPLES

The present invention will now be further shown by, but is by no means limited to, the following examples.

EXAMPLE 1

Step (1)

Cells of *Lithospermum erythrorhizon Seib. et Zucc.* were cultured in a liquid culture medium of Linsmaier and Skoog (1965). The cultured cells were then treated in the following aqueous solution, having an osmotic pressure of 16 kg/cm$^2$ and containing cell wall decomposing enzymes, at 30° C. for 2 hours to prepare the protoplasts.

Composition of aqueous solution for cell wall decomposition
2.5% Cellulose "Onozuka" R-10 (Kinki Yakult)
1.0% Driserase (Kyowa Ferm.)
0.5% Macerozyme R-10 (Kinki Yakult)
0.6M/l Glucose
5 mM/l Calcium chloride
5 mM/l Magnesium chloride The resultant protoplasts were suspended in a glucose solution having an osmotic pressure of 16 kg/cm$^2$ (0.6M/l glucose, 5 mM/l calcium chloride, 5 mM/l magnesium chloride), and the density of the protoplasts in the suspension was adjusted to 2×10$^6$ cells/ml. A 20 μl amount of the suspension was put dropwise on a Petri dish having a diameter of 5 cm (Falcon).

Step (2)

The Petri dish was let to stand for 5 minutes, then 20 μl of an aqueous solution of polyethylele glycol (50% by weight polyethylene glycol having a molecular weight of about 4000, 50 mM/l calcium chloride, 250 mM/l glucose) was added to the protoplast suspension on the Petri dish. The Petri dish was let to stand for 10 minutes at a temperature of 25° C.

Step (3)

Then, 6 ml of an alkaline aqueous solution of calcium chloride having an osmotic pressure of 6 kg/cm$^2$ (50 mM/l calcium chloride, 50 mM/l glucose, pH 10.5) was added to the protoplast suspension on the Petri dish at a rate of 0.2 ml/min. After the addition, the osmotic pressure became about 6 kg/cm$^2$. Then, the Petri dish was let to stand for 10 minutes at a temperature of 25° C.

The number of fused protoplasts was counted microscopically, and the ratio of the fused protoplasts (cell fusion rate) was calculated as follows:

$$\text{Cell fusion rate} = \frac{\text{Number of fused protoplasts}}{\text{Number of protoplasts before fusion}} \times 100$$

The cell fusion rate was 50%.
The survival rate of cells after the treatment was 78%.

EXAMPLE 2

A procedure similar to Example 1 was carried out, except that, in step (3), aqueous solutions shown in Table 1 were used instead of the alkaline aqueous solution of calcium chloride having an osmotic pressure of 6 kg/cm$^2$ (pH 10.5).

TABLE I

| Aqueous solution | Osmotic pressure (kg/cm$^2$) | Cell fusion rate (%) |
| --- | --- | --- |
| Calcium chloride | 6 | 60 |
| Magnesium chloride | 6 | 34 |
| Glucose | 6 | 20 |
| Linsmaier and Skoog Med. | 5 | 25 |

Fused protoplasts obtained from the aqueous solution of calcium chloride having an osmotic pressure of 6 kg/cm$^2$ were then cultivated. Within two weeks, the fused protoplasts regenerated cell walls on their surface, and began to divide.

EXAMPLE 3

A procedure similar to Example 1 was carried out, except that in step (3), an alkaline aqueous solution of calcium chloride having an osmotic pressure of 9 kg/cm$^2$ (pH 10.5) was used instead of the alkaline aqueous solution of calcium chloride having an osmotic pressure of 6 kg/cm$^2$ (pH 10.5).

The cell fusion rate was 30%.

EXAMPLE 4 (COMPARATIVE EXAMPLE)

A procedure similar to Example 1 was carried out, except that, in step (3), an alkaline aqueous solution of calcium chloride having an osmotic pressure of 14 kg/cm$^2$ (pH 10.5) was used instead of the alkaline aqueous solution of calcium chloride having an osmotic pressure of 6 kg/cm$^2$ (pH 10.5).

The cell fusion rate was 3%.

EXAMPLE 5 (COMPARATIVE EXAMPLE)

A procedure similar to Example 1 was carried out, except that, in step (3), an alkaline aqueous solution of calcium chloride having an osmotic pressure of 16 kg/cm$^2$ (pH 10.5) was used instead of the alkaline aqueous solution of calcium chloride having an osmotic pressure of 6 kg/cm$^2$ (pH 10.5).

The cell fusion rate was 0%.

EXAMPLE 6 (COMPARATIVE EXAMPLE)

A procedure similar to Example 5 was carried out, except that, in step (3), after the addition of the alkaline aqueous solution of calcium chloride having.an osmotic pressure of 16 kg/cm$^2$, the treatment shown in Table 2 was conducted.

The results are shown in Table 2.

TABLE 2

| Treatment | Cell fusion rate (%) |
| --- | --- |
| Centrifuging (70 XG, 5 min.) | 0 |
| High temperature (40° C., 3 min.) | 0 |
| Addition of N—ethylmaleimide (20 mM/l) | 0 |

EXAMPLE 7

A procedure similar to Example 1 was carried out, except that, in step (3), an alkaline aqueous solution of calcium chloride containing 0.1 (W/V) % of bovine serum albumin and having an osmotic pressure of 6 kg/cm$^2$ (50 mM/l calcium chloride, 50 mM/l glucose, pH 10.5) was used instead of the alkaline aqueous solution of calcium chloride having an osmotic pressure of 6 kg/cm$^2$.

The cell fusion rate was 62%.

The survival rate was 85%.

EXAMPLE 8

A procedure similar to Example 1 was carried out, except that, in step (3), an alkaline aqueous solution of calcium chloride containing 0.5 (W/V) % of globulin and having an osmotic pressure of 6 kg/cm$^2$ (pH 10.5) was used instead of the alkaline aqueous solution of calcium chloride having an osmotic pressure of 6 kg/cm$^2$ (pH 10.5).

The cell fusion rate was 60%.

EXAMPLE 9

A procedure similar to Example 1 was carried out, except that, in step (3), an alkaline aqueous solution of calcium chloride containing 1.0 (W/V) % of a colloidal synthetic polymer prepared by coating colloidal silica with polyvinyl pyrrolidone (commercially provided by Pharmacia Japan Co. as Fercoll TM), and having an osmotic pressure of 6 kg/cm$^2$ (pH 10.5) was used instead of the alkaline aqueous solution of calcium chloride having an osmotic pressure of 6 kg/cm$^2$ (pH 10.5).

The cell fusion rate was 54%. The survival rate was 88%.

EXAMPLE 10

A procedure similar to Example 1 was carried out, except that, in step (3), an alkaline aqueous solution of calcium chloride containing 1% by volume of dimetyl sulfoxide and having an osmotic pressure of 9 kg/cm$^2$ (50 mM/l calcium chloride, 50 mM/l glucose, pH 10.5) was used instead of the alkaline aqueous solution of calcium chloride having an osmotic pressure of 6 kg/cm$^2$.

The cell fusion rate was 57%.

EXAMPLE 11 (COMPARATIVE EXAMPLE)

A procedure similar to Example 1 was carried out, except that, in step (3), an alkaline aqeos solution of calcium chloride containing a 1% by volume of di- methyl sulfoxide and having an osmotic pressure of 14 kg/cm$^2$ (50 mM/l calcium chloride, 260 mM/l glucose, pH 10.5) was used instead of the alkaline aqueous solution of calcium chloride having an osmotic pressure of 6 kg/cm$^2$ (pH 10.5).

The cell fusion rate was 11%.

EXAMPLE 12 (COMPARATIVE EXAMPLE)

A procedure similar to Example 1 was carried out, except that, in step (3), an alkaline aqueous solution of calcium chloride containing 1% by volume of dimethyl- formamide and having an osmotic pressure of 14 kg/cm$^2$ (50 mM/l calcium chloride, 250 mM/l glu- close, pH 10.5) was used instead of the alkaline aqueous solution of calcium chloride having an osmotic pressure of 6 kg/cm$^2$ (pH 10.5).

The cell fusion rate was 9%.

EXAMPLE 13

Step (1)

Protoplasts were prepared from mesophyll of *Nicotinia tabacum* L. var. *Samsun* grown at room temperature according to the method reported by Toshiyuki Nagata and Itaru Tateba in "Planta" Vol., 99 (1971), pg 12.

The resultant protoplasts were suspended in an aqueous solution of mannitol having an osmotic pressure of 13 kg/cm$^2$ (0.5 M/l mannitol, 5 mM/l calcium chloride, 5 mM/l magnesium chloride), then the density of the protoplasts in the suspension was adjusted to 10$^6$ cells/ml. A 30 μl amount of the suspension was then put dropwise on a Petri dish having a diameter of 5 cm (Falcon).

Step (2)

The Petri dish was let to stand for 10 minutes, then 30 μl of an aqueous solution of polyethylene glycol (70% by weight polyethylene glycol 1540, 10 mM/l calcium chloride, 120 mM/l glucose) was added to the protoplast suspension on the Petri dish. The Petri dish was let to stand for 15 minutes at a temperature of 25° C.

Step (3)

Then, 9 ml of an alkaline aqueous solution of calcium chloride having an osmotic pressure of 9 kg/cm$^2$ (50 mM/l calcium chloride, 90 mM/l glucose, pH 10.5) was added to the protoplast suspension on the Petri dish at a rate of 0.3 ml/min. After the addition, the osmotic pressure became about 9 kg/cm$^3$. Then, the Petri dish was let to stand for 15 minutes at a temperature of 25° C.

After that, the cell fusion rate was obtained in the same manner as in Example 1.

The cell fusion rate was 40%.

EXAMPLE 14 (COMPARATIVE EXAMPLE)

A procedure similar to Example 13 was carried out, except that, in step (3), an alkaline aqueous solution of calcium chloride having an osmotic pressure of 13 kg/cm$^2$ (pH 10.5) was used instead of the alkaline aqueous solution of calcium chloride having an osmotic pressure of 9 kg/cm$^2$ (pH 10.5).

The cell fusion rate was 8%.

EXAMPLE 15

A procedure similar to Example 13 was carried out, except that, in step (3), an alkaline aqueous solution of calcium chloride containing 0.2 (W/V) % of bovine serum albumin and having an osmotic pressure of 9 kg/cm$^2$ (50 mM/l calcium chloride, 90 mM/l glucose, pH 10.5) was used instead of the alkaline aqueous solution of calcium chloride having an osmotic pressure of 9 kg/cm$^2$.

The cell fusion rate was 51%.

EXAMPLE 16

A procedure similar to Example 13 was carried out, except that, in step (3), an alkaline aqueous solution of calcium chloride containing 1.0 (W/V) % of a colloidal polymer prepared from sucrose and epichlorohydrin (commercially provided by Pharmacia Japan Co. as "Ficoll") and having an osmotic pressure of 9 kg/cm$^2$ (pH 10.5) was used instead of the alkaline aqueous solution of calcium chloride having an osmotic pressure of 9 kg/cm$^2$.

The cell fusion rate was 50%. The survival rate after the treatment was 87%.

EXAMPLE 17

A procedure similar to Example 13 was carried out, except that, in step (3), an alkaline aqueous solution of calcium chloride containing 1% by volume of dimethyl sulfoxide and having an osmotic pressure of 9 kg/cm$^2$ (50 mM/l calcium chloride, 50 mM/l glucose, pH 10.5) was used instead of the alkaline aqueous solution of

EXAMPLE 18

Step (1)

Cells of *Coptis japonica Makino* were cultured in a liquid culture medium in Linsmaier and Skoog (1965). The cultured cells were then treated in the following aqueous solution, having an osmotic pressure of 19 kg/cm$^2$ and containing cell wall decomposing enzymes, for 4 hours at a temperature of 25° C. to prepare the protoplasts.

Composition of aqueous solution for cell wall decomposition
3.0% Cellulase "Onozuka" R-10 (Kinki Yakult)
0.5% Driselase (Kyowa Ferm.)
0.5% Macerozyme R-10 (Kinki Yakult)
0.7 M/l Sorbitol
5 mM/l Calcium chloride
5 mM/l Magnesium chloride The resultant protoplasts were suspended in an aqueous solution of sorbitol having an osmotic pressure of 19 kg/cm$^2$ (0.7M/l sorbitol, 5 mM/l calcium chloride, 5 mM/l magnesum chloride). The density of the protoplasts in the suspension was adjusted to $5 \times 10^3$ cells/ml. A 10 μl amount of the suspension was then put dropwise on a Petri dish having a diameter of 5 cm (Falcon).

Step (2)

The Petri dish was let to stand for 5 minutes, then 10 μl of an aqueous solution of polyethylene glycol (30% by weight polyethylene glycol 7500, 10 mM/l calcium chloride, 450 mM/l sorbitol) was added to the protoplast suspension on the Petri dish. The Petri dish was let to stand for 10 minutes at a temperature of 25° C.

Step (3)

Then, 3 ml of an aqueous solution of calcium chloride having an osmotic pressure of 3 kg/cm$^2$ (50 mM/l calcium chloride) was added to the protoplast suspension on the Petri dish at a rate of 0.1 ml/min. After the addition, the osmotic pressure became about 3 kg/cm$^2$. Then, the Petri dish was let to stand for 5 minutes at a temperature of 25° C.

After that, the cell fusion rate was obtained in the same manner as in Example 1.

The cell fusion rate was 10%.

EXAMPLE 19 (COMPARATIVE EXAMPLE)

A procedure similar to Example 18 was carried out, except that, in step (3), an aqueous solution fo calcium chloride having an osmotic pressure of 19 kg/cm$^2$ was used instead of the aqueous solution of calcium chloride having an osmotic pressure of 3 kg/cm$^3$.

The cell fusion rate was 1%.

EXAMPLE 20

A procedure similar to Example 18 was carried out, except that, in step (3), an aqueous solution of calcium chloride containing 0.1 (W/V) % of bovine rerum albumin and having an osmotic pressure of 3 kg/cm$^2$ (50 mM/l calcium chloride) was used instead of the aqueous solution of calcium chloride having an osmotic pressure of 3 kg/cm$^2$.

The cell fusion rate was 14%.

EXAMPLE 21

Step (1)

Cells of each plant of *Lithospermum erythrorhizon Seib. et Zucc.* and *Dianthus Caryophyllus L.* were separately cultured in a liquid culture medium of Linsmaier and Skogg (1965). The cultured cells of each plant were separately treated in the aqueous solution, containing cell wall decomposing enzymes described in Example 1, for 3 hours at a temperature of 30° C. to prepare the protoplasts.

The resultant protoplasts of each plant were separately suspended in an aqueous solution of glucose having an osmotic pressure of 16 kg/cm$^2$ (0.6M/l gluclose, 5 mM/l calcium chloride, 5 mM/l magnesium chloride). The density of the protoplasts of each plant in the suspension was separately adjusted to 10$^6$ cells/ml, and the two suspensions were mixed together. A 20 μl amount of the mixed suspension was then put dropwise on a Petri dish having a diameter of 5 cm (Falcon).

Step (2)

The Petri dish was let to stand for 5 minutes, then 20 μl of an aqueous solution of polyethylene glycol (50% by weight polyethylene glycol 4000, 50 mM/l calcium chloride, 250 mM/l glucose) was added to the protoplast suspension on the Petri dish. The Petri dish was let to stand for 10 minutes at a temperature of 25° C.

Step (3)

Then, 6 ml of an alkaline aqueous solution of calcium chloride having an osmotic pressure of 6 kg/cm$^2$ (50 mM/l calcium chloride, 50 mM/l glucose, pH 10.5) was added to the protoplast suspension on the Petri dish at a rate of 0.2 ml/min. After the addition, the osmotic pressure became about 6 kg/cm$^2$. Then, the Petri dish was let to stand for 10 minutes at a temperature of 25° C.

Thus, new hybrid protoplasts derived from protoplasts of *Lithospermum erythrorhizon Seib. et Zucc.* and *Dianthus caryophylllus L.* by fusion were obtained.

After that, the cell fusion rate was obtained in the same manner as in Example 1.

The cell fusion rate of the hybrid protoplasts was 40%.

EXAMPLE 22 (COMPARATIVE EXAMPLE)

A procedure similar to Example 21 was carried out, except that, in step (3), an alkaline aqueous solution of calcium chloride having an osmotic pressure of 16 kg/cm$^2$ (pH 10.5) was used instead of the alkaline aqueous solution of calcium chloride having an osmotic pressure of 6 kg/cm$^2$ (pH 10.5).

The cell fusion rate was 0%.

EXAMPLE 23

A procedure similar to Example 21 was carried out, except that, in step (3), an alkaline aqueous solution of calcium chloride containing 0.5 (W/V) % of bovine serum albumin and having an osmotic pressure of 6 kg/cm$^2$ (50 mM/l calcium chloride, 50 mM/l gluclose, pH 10.5) was used instead of the alkaline aqueous solution of calcium chloride having an osmotic pressure of 6.5 kg/cm.

The cell fusion rate of the hybrid protoplasts was 53%.

EXAMPLE 24

A procedure similar to Example 21 was carried out, except that, in step (3), an alkaline aqueous solution of calcium chloride containing 2.0 (W/V) % of a colloidal synthetic polymer prepared by coating a surface of colloidal silica with polyvinyl-pyrrolidone (commercially provided by Pharmacia Japan Co. as Fercoll ™) and having an osmotic pressure of 6 kg/cm$^2$ (pH 10.5) was used instead of the alkaline aqueous solution having an osmotic pressure of 6 kg/cm$^2$ (pH 10.5).

The cell fusion rate of the hybrid protoplasts was 45%.

EXAMPLE 25

A procedure similar to Example 21 was carried out, except that, in step (3), an alkaline aqueous solution of calcium chloride containing 1.0% by volume of dimetyl formamide and having an osmotic pressure of 6 kg/cm$^2$ (50 mM/l calcium chloride, 50 mM/l glucose, pH 10.5) was used instead of the alkaline solution of calcium chloride having an osmotic pressure of 6 kg/cm$^2$.

The cell function rate of the hybrid protoplasts was 48%.

EXAMPLE 26

Step (1)

Cells of each plant of *Lithospermum etythrorhizon Seib. et Zucc.* and *Duboisia leichhardtii F. Muell* were separately cultured in a liquid culture medium of Linsmaier and Skoog (1965). The cultured cells of the each plant were separately treated in the aqueous solution containing cell wall decomposing enzymes described in Example 1 for 2 hours at a temperature of 30° C. to prepare the protoplasts.

The resultant protoplasts of each plant were separately suspended in an aqueous solution of glucose having an osmotic pressure of 16 kg/cm$^2$ (0.6M/l glucose, 5 mM/l calcium chloride, 5 mM/l magnesium chloride). The density of the protoplasts of each plant in the suspension was separately adjusted to $5 \times 10^6$ cells/ml, and the two suspensions were mixed together. A 10 μl amount of the mixed suspension was then put dropwise on a Petri dish having a diameter of 5 cm (Falcon).

Step (2)

The Petri dish was let to stand for 10 minutes, then 10 μl of an aqueous solution of polyvinyl alcohol (20% by weight polyvinyl alcohol 500, 10 mM/l calcium chloride, 300 mM/l glucose) was added to the protoplast suspension on the Petri dish. The Petri dish was let to stand for 10 minutes at a temperature of 25° C.

Step (3)

Then, 12 ml of an aqueous solution of calcium chloride having an osmotic pressure of 9 kg/cm$^2$ (70 mM/l calcium chloride, 50 mM/l glucose) was added to the protoplastc suspension on the Petri dish at a rate of 0.2 ml/min. After the addition, the osmotic pressure became about 9 kg/cm$^2$. Then, the Petri dish was let to stand for 20 minutes at a temperature of 25° C.

Thus, new hybrid protoplasts derived from protoplasts of *Lithospermum etythrorhizon Seib. et Zucc.* and *Duboisia leichhardtii F. Muell* by fusion were obtained.

After that, the cell fusion rate was obtained in the same manner as in Example 1.

The cell fusion rate of the hybrid protoplasts was 20%.

EXAMPLE 27 (COMPARATIVE EXAMPLE)

A procedure similar to Example 26 was carried out, except that, in step (3), an aqueous solution of calcium chloride having an osmotic pressure of 16 kg/cm$^2$ was used instead of the aqueous solution of calcium chloride having an osmotic pressure of 9 kg/cm$^2$.

The cell fusion rate was 0%.

We claim:

1. A method for promoting fusion of plant protoplasts comprising the steps of:
   (a) treating the plant protoplasts with a fusion agent in an aqueous solution comprising said fusion agent at an osmotic pressure of 12 to 40 kg/cm$^2$,
   (b) incubating the resultant plant protoplasts in an incubation medium having an osmotic pressure of 2 to 10 kg/cm$^2$ for a period of 5 minutes to 48 hours;
   (c) separating the protoplasts from the incubation medium and transferring the protoplasts to a culture medium having an osmotic pressure necessary to maintain the protoplasts in a stable form.

2. A method as claimed in claim 1, wherein protoplasts of at least one plant selected from the group consisting of genera Lithospermus, Nicotinia, Coptis, Dianthus, Duboisia, Rosa, Oryza, Triticum, and Zea are fused.

3. A method as claimed in claim 2, wherein the fusion is carried out between plant protoplasts of the same genus.

4. A method as claimed in claim 2, wherein the fusion is carried out between plant protoplasts of different genera.

5. A method as claimed in claim 1, wherein the fusion agent is selected from the group consisting of polyethylene glycol, polypropylene glycol, polyvinyl alcohol, dextrin, pectin, calcium chloride, sodium nitrate, and a mixture thereof.

6. A method as claimed in claim 1, wherein an incubation time is not more than 48 hours.

7. A method as claimed in claim 1, wherein the incubation medium comprises at least one material selected from the group consisting of sucrose, glucose, mannitol, sorbose, calcium chloride, and magnesium chloride.

8. A method as claimed in claim 1, wherein the incubation medium comprises at least one fusion promoting agent selected from the group consisting of water-soluble proteins and hydrophilic colloidal synthetic polymers.

9. A method as claimed in claim 8, wherein the water-soluble proteins are selected from the group consisting of albumin, globulin, papain, and bromelin.

10. A method as claimed in claim 8, wherein the hydrophilic colloidal synthetic polymers are prepared by coating at least one hydrophilic resin selected from the group consisting of polyvinyl-pyrrolidone and polyacrylamide on fine particles of at least one insoluble material selected from the group consisting of glass, silica, alumina and active carbon.

11. A method as claimed in claim 8, wherein the hydrophilic colloidal synthetic polymers are prepared from sucrose and epichlorohydrin and have a plurality of branched structures.

12. A method as claimed in claim 8, wherein the incubation medium comprises the fusion promoting agent in an amount of 0.001 to 10 parts by weight, per 100 parts by weight of the incubation medium containing the plant protoplasts.

13. A method as claimed in claim 1, wherein the incubation medium comprises at least one fusion promoting agent selected from the group consisting of water-soluble aprotic polar compounds.

14. A method as claimed in claim 13, wherein the water-soluble aprotic polar compound is selected from the group consisting of: sulforane, dimethyl sulfone, dimethyl sulfoxide, diethyl sulfoxide, N,N-dimethylformamide, N,N-diethylformamide, N,N-dimethylacetamide, N-methylpyrrolidone, N-ethylpyrrolidone, N-isopropylpyrrolidone, N-octylpyrrolidone, N-cyclohexylpyrrolidone, N-benzylpyrrolidone, polyvinyl-pyrrolidone, N-methyl-2-pyridine, N-methyloxazolidone, hexamethylphosphoric triamide, and hexaethylphosphoric triamide.

15. A method as claimed in claim 13, wherein the incubation medium comprises the fusion promoting agent in an amount of 0.01 to 10 parts by volume, per 100 parts by volume of the incubation medium containing the protoplasts.

* * * * *